United States Patent [19]

Walloch

[11] Patent Number: 5,505,206
[45] Date of Patent: Apr. 9, 1996

[54] METHOD AND APPARATUS FOR EXCLUDING ARTIFACTS FROM AUTOMATIC BLOOD PRESSURE MEASUREMENTS

[75] Inventor: Richard A. Walloch, Aloha, Oreg.

[73] Assignee: SpaceLabs Medical, Inc., Redmond, Wash.

[21] Appl. No.: 96,602

[22] Filed: Jul. 22, 1993

Related U.S. Application Data

[63] Continuation of Ser. No. 774,661, Oct. 11, 1991, Pat. No. 5,253,648.

[51] Int. Cl.⁶ .................................................. A61B 5/02
[52] U.S. Cl. .................................. 128/681; 128/682
[58] Field of Search .......................... 128/677, 680–686

[56] References Cited

U.S. PATENT DOCUMENTS

| 4,223,681 | 9/1980 | Sherman | 128/672 |
| 4,349,034 | 9/1982 | Ramsey, III | 128/681 |
| 4,360,029 | 11/1982 | Ramsey, III | 128/681 |
| 4,592,366 | 5/1986 | Sainomoto et al. | 128/680 |
| 5,014,714 | 5/1991 | Millay et al. | 128/680 |

FOREIGN PATENT DOCUMENTS

0207807A3  1/1987  European Pat. Off. .......... A61B 5/02

*Primary Examiner*—Angela D. Sykes
*Assistant Examiner*—Robert L. Nasser, Jr.
*Attorney, Agent, or Firm*—Seed and Berry

[57] ABSTRACT

A method and system for detecting blood pressure pulses and screening out artifact-induced pulses when an automatic blood pressure monitor is provided. In preferred embodiments, the system detects the occurrence of an oscillometric pulse, determines the amplitude and rise time of the pulse, determines whether the amplitude and rise-times are within patient-specific screening limits and disregards pulses not within the limits, determines whether a pulse matches other pulses and saves the matching pulse data, determines the diastolic and systolic pressure based on the saved matched pulse data, and updates the patient-specific screening limits. In a preferred embodiment, pulses match based on similar amplitude and rise time characteristics. The amplitude and rise time screening limits are updated based on average values of prior blood pressure measurements for the patient.

11 Claims, 6 Drawing Sheets

METHOD AND APPARATUS FOR EXCLUDING ARTIFACTS FROM AUTOMATIC BLOOD PRESSURE MEASUREMENTS

This application is a continuation of U.S. application Ser. No. 07/774,661, filed Oct. 11, 1991, now U.S. Pat. No. 5,253,648.

TECHNICAL FIELD

This invention relates to the automatic measurement of blood pressure, and more particularly to a method and apparatus for detecting blood pressure pulses and screening out artifact-induced pulses.

BACKGROUND OF THE INVENTION

Automatic blood pressure monitors are commonly used to periodically measure the blood pressure of a patient. In most automatic blood pressure monitors, a pressure cuff is attached to a patient's arm over the brachial artery. The cuff is first pressurized with an applied pressure that is high enough to substantially occlude the brachial artery. The cuff pressure is then gradually reduced, either continuously or in increments. As the pressure is reduced to systolic pressure, the flow of blood through the brachial artery beneath the cuff increases substantially.

When the blood flows through the brachial artery following each contraction of the heart, it imparts a pulsatile movement to the wall of the artery. This pulsatile movement is coupled to a blood pressure cuff extending over the artery as minute changes in the cuff pressure, which are known as oscillometric pulses. Automatic blood pressure monitors measure and record the amplitude of the oscillometric pulses at a number of cuff pressures. After the blood pressure measurement had been completed, a table contains the oscillometric pulse amplitudes recorded at each cuff pressure.

In theory, the systolic, diastolic, and mean arterial blood pressures can then be determined from the values in the table using empirical definitions of these parameters as a function of the amplitudes of these oscillometric pulses. However, blood pressure measurements are often adversely affected by artifact, generally produced by patient movement. Motion-induced artifacts can substantially alter the measured amplitude of oscillometric pulses thus introducing inaccuracies in the measurement of the patient's blood pressure.

Prior systems use various techniques to minimize the effects of artifacts. Some prior systems screen oscillometric pulses based on their amplitude. Pulses with amplitudes outside the screen are considered artifact-induced. The screen is generally a population-based screen and not specific to any patient. Some previous systems also compare sequential pulses to ensure they are blood pressure induced. If two sequential pulses have similar amplitudes, these systems assume the pulse is blood pressure induced. However, these screening and comparison techniques do not always produce acceptable results. It would be desirable to have a system in which the screening and comparing of pulses more accurately identifies blood pressure induced pulses.

SUMMARY OF THE INVENTION

It is an object of the present invention to provide an improved method and system for detecting blood pressure induced pulses in an automatic blood pressure measurement device.

It is another object of the present invention to provide a method and system in which oscillometric pulses are matched based on the amplitude and rise time characteristics of the pulses.

It is another object of the present invention to provide a method and system in which artifact-induced pulses can be detected by the use of patient-specific amplitude and rise time screening limits.

It is another object of the present invention to provide a method and system in which the patient-specific screening limits are automatically updated based on data gathered during the blood pressure measurement process.

These and other objects, which will become apparent as the invention is more fully described below, are obtained by an improved blood pressure measurement device. In preferred embodiments, the device detects the occurrence of an oscillometric pulse, determines the amplitude and rise time of the pulse, determines whether the amplitude and rise time are within patient-specific screening limits and disregards pulses not within the limits, determines whether a pulse matches other pulses and saves the matching pulse data, determines the diastolic and systolic pressure based on the saved matched pulse data, and updates patient-specific screening limits. In a preferred embodiment, pulses match based on similar amplitude and rise time characteristics. The amplitude and rise time screening limits are updated based on average values of prior blood pressure measurements for the patient.

DETAILED DESCRIPTION OF THE INVENTION

Figure 1:
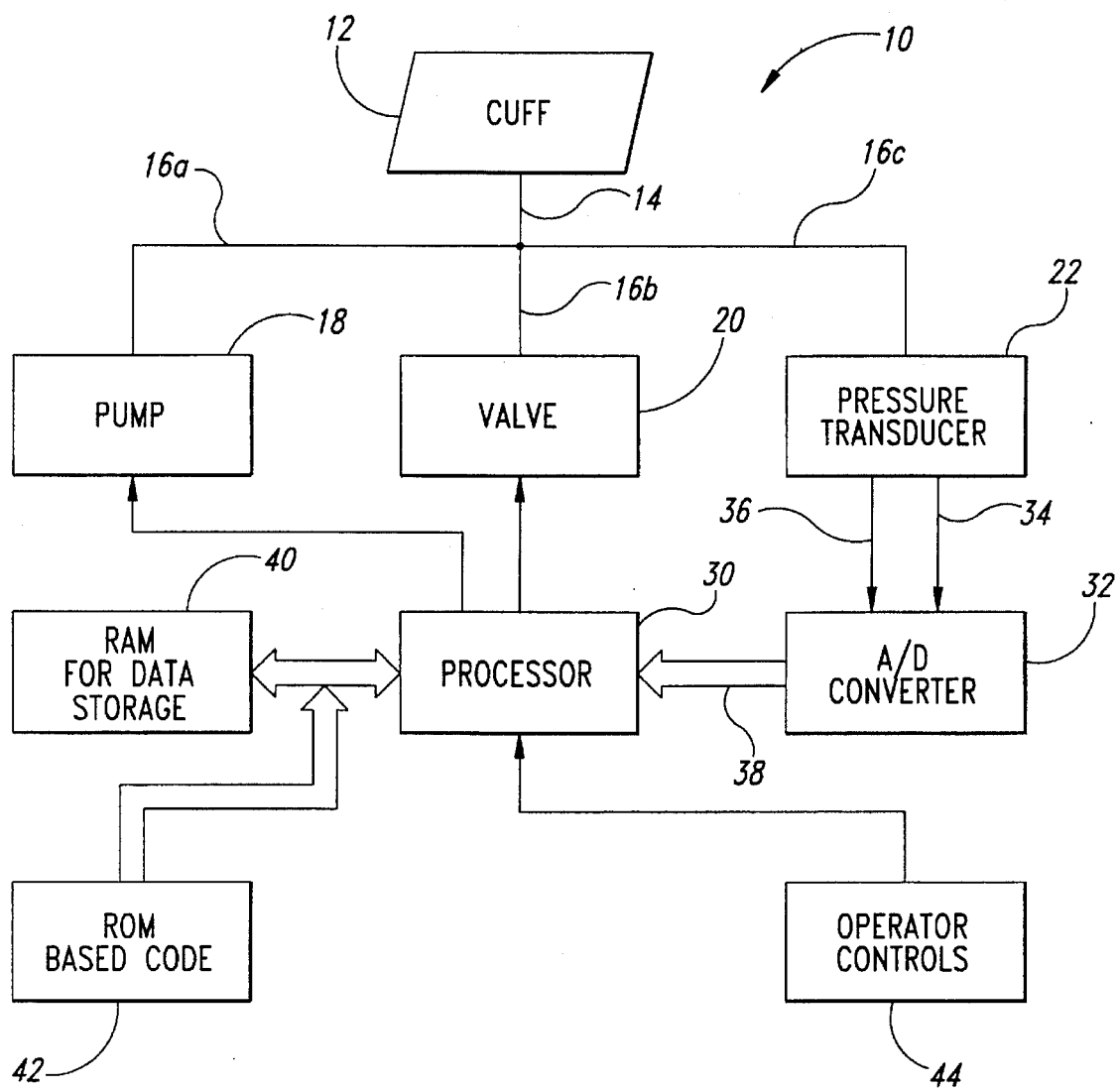
FIG. 1 is a block diagram of an automatic blood pressure monitor for detecting blood pressure pulses and screening out artifact-induced pulses.

One embodiment of a system for detecting blood pressure pulses and screening out artifact-induced pulses in an automatic blood pressure measuring system is illustrated in FIG. 1. The system 10 comprises a number of hardware components, all of which are conventional. The system includes a conventional blood pressure cuff 12 in fluid communication with conduits 14 and 16, a conventional pump 18, a conventional valve 20, and a conventional pressure transducer 22. The pump 18 and valve 20 are operated by a conventional microprocessor 30.

As explained in greater detail below, during the operation of the automatic blood pressure measuring system, the blood pressure cuff 12 is inflated to a pressure that is greater than systole as indicated by the pressure transducer 22. The valve 20 is then opened, usually for a predetermined period, although it may be continuously open to allow a slight leakage of air from the blood pressure cuff 12. However, the valve 20 normally allows air to escape from the cuff 12 fairly rapidly in relatively small increments. As the pressure in the cuff 12 is reduced, either gradually or incrementally, the pressure in the cuff 12 is measured by the pressure transducer 22.

The pressure in the blood pressure cuff 12 consists of two components, namely, a relatively constant, or "DC," component and a relatively variable, or "AC," component. The relatively constant component is a function of the pressure in the blood pressure cuff 12. The relatively variable component is produced by the minute change in the pressure of the cuff 12 following each contraction of the heart. Thus, the relatively constant DC component of the pressure in the cuff can be used as an indication of cuff pressure, while the relatively variable AC component of the pressure in the cuff 12 can be used as an indication of an oscillometric pulse.

Two signals are obtained from the pressure transducer 22. One set of circuitry 34 supplies a DC component to an analog-to-digital (A/D) converter 32. Anther set of circuitry 36 supplies an AC component to the A/D converter 32. The signal supplied through the DC circuitry 34 is thus an indication of the cuff pressure, while the signal supplied through the AC circuitry 36 is an indication of the oscillometric pulse. The A/D converter 32 digitizes the DC and the AC signals and outputs digital bytes indicative of their values through a bus 38 to the microprocessor 30.

As mentioned above, the microprocessor 30 is of conventional variety and, as is typical with such devices, is connected to a random access memory 40 used for the storage of data, and to either random access memory or read-only memory 42 that contains the software for operating the microprocessor 30. Operator controls 44, such as a keyboard or buttons, are also connected to the microprocessor 30.

Although the measuring system 10 illustrated in FIG. 1 utilizes a pressure transducer 22 and separate circuitry for the AC and the DC pressure signals, it will be understood that other implementations are possible. For example, a single circuit providing a signal corresponding to both the steady-state and the variable pressures in the cuff 12 can be supplied to the analog-to-digital converter 32. After the signal is digitized by analog-to-digital converter 32 and applied to the microprocessor 30, algorithms executed by the microprocessor 30 can detect the steady-state component of the cuff pressure and the variable component variations in the cuff pressure.

In a preferred embodiment, the present invention is used to periodically determine the systolic and diastolic blood pressure of a patient. To determine the systolic and diastolic blood pressure, the preferred system of the present invention collects blood pressure readings at several cuff pressures, referred to as target pressure levels. When the cuff is inflated or deflated to the target pressure, the system samples the output of the A/D converter 32 to determine when an oscillometric pulse occurs. The occurrence of an oscillometric pulse is detected when the signal applied to the A/D converter 32 has predetermined characteristics, as described in greater detail below. The system then determines whether these pulses are within pulse amplitude and rise time screening limits. If an oscillometric pulse is not within the screening limits, it is disregarded. The screening limits for the patient are updated after the systolic and diastolic blood pressure are determined. This effects the automatic updating of patient-specific screening limits. The system collects data on pulses at a particular target pressure level until two matching pulses are detected. Pulses match when they have similar amplitude and rise time characteristics. When a match is found, the system saves the matching pulse data. The system collects matching pulse data for various target pressure levels. The system then evaluates the matching pulse data to determine the systolic and diastolic pressure. Algorithms to determine the systolic and diastolic blood pressures are well-known as are various algorithms to reduce the effects of artifacts. An algorithm to determine systole and diastole is described in U.S. Pat. No. 4,785,820 entitled Method And Apparatus For Systolic Blood Pressure Measurements, which is incorporated herein by reference. Algorithms to reduce the effects of artifacts are described in U.S. Pat. No. 4,777,959 entitled Artifact Detection Based On Heart Rate In A Method And Apparatus For Indirect Blood Pressure Measurement and U.S. Pat. No. 5,014,714 entitled Method And Apparatus For Distinguishing Between Accurate And Inaccurate Blood Pressure Measurements In The Presence Of Artifact, which are hereby incorporated by reference. If the system successfully determines systolic and diastolic blood pressure, the system then updates the screening limits.

Figure 2:
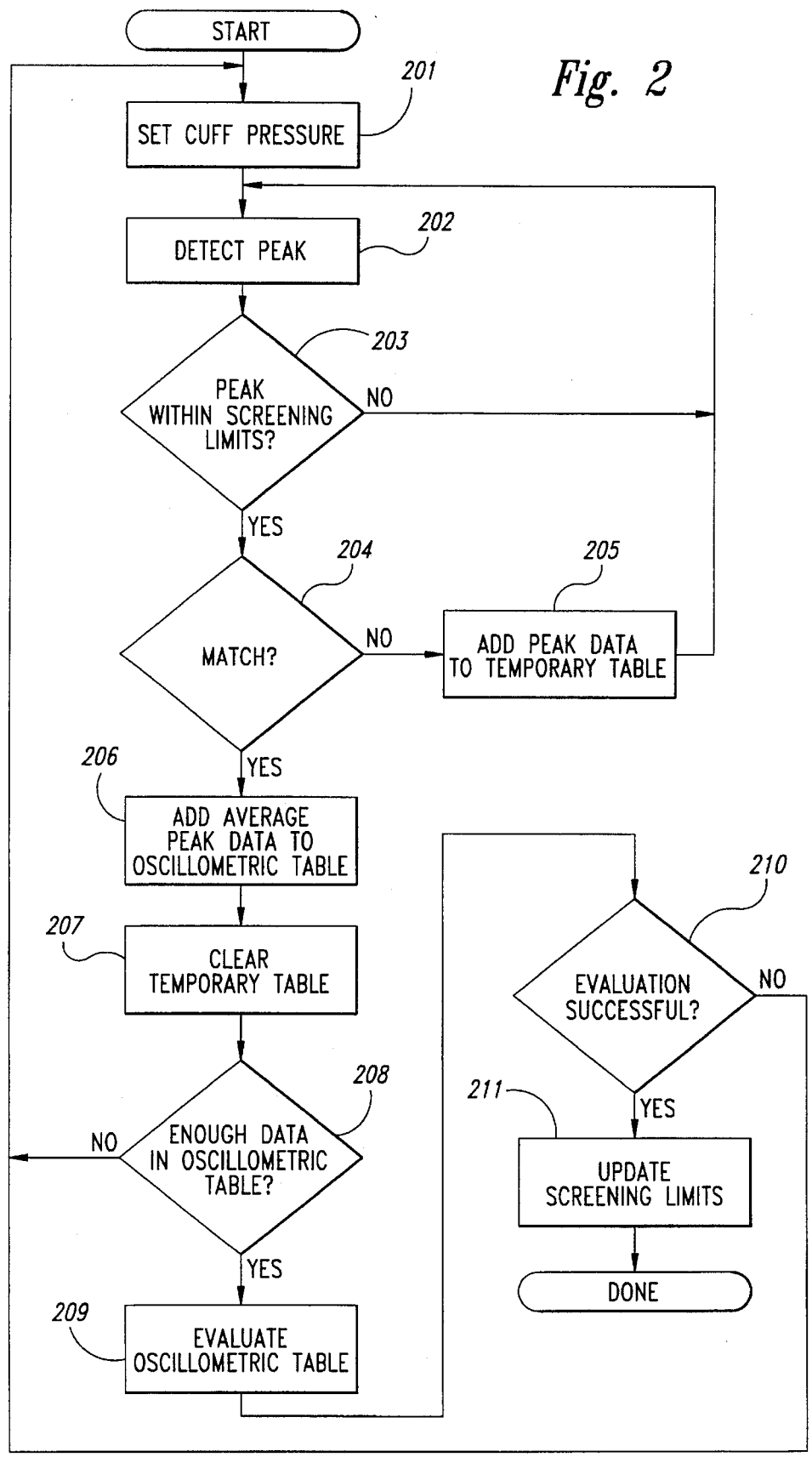
FIG. 2 is a flow diagram of an overview of the processing of the present invention.

FIG. 2 is a flow diagram of an overview of the processing of the present invention. In a preferred embodiment, the processing is implemented on a computer program, which executes on microprocessor 30. In block 201, the system sets the cuff pressure to the target pressure. In a preferred embodiment, the target pressure is initially set in excess of the anticipated systolic pressure. The target pressure is then decremented sequentially. In block 202, the system waits until the interrupt routine detects a peak in the oscillometric data. A peak usually indicates that a pulse has occurred, although a peak could be produced by an artifact. In a preferred embodiment, a peak is detected when the AC pressure is increasing and passes through a "high trigger" level and then passes through a "low trigger" level while decreasing. In block 203, the system determines whether the detected pulse is within the screening limits. In a preferred embodiment, the screening limits are patient-specific limits based on the amplitude and the rise time of the pulse. In alternate embodiments, the pulse fall time, pulse width, integral of the pulse, and derivatives of the pulse can be used as screening limits (and for matching pulses as discussed below). If the pulse data is within the screening limits, then the system continues at block 204, else the system disregards the pulse data and loops back to block 202 to await the next peak. The system maintains a Temporary Table of pulse data that is collected at a particular target pressure and that is within the screening limits. In block 204, the system determines whether the current pulse data matches any of the data stored in the Temporary Table. In a preferred embodiment, a match is detected based on the amplitude and the rise time of the pulses. If a match is detected with any of the pulse data in the Temporary Table, the system continues at block 206, else the system adds the current pulse data to the Temporary Table in block 205 and loops to block 202 to detect the next peak. The system maintains an Oscillometric Table that contains the DC pressure, AC pressure, rise time, and heart rate associated with each matched pulse. (The rise time is used to update the screening limits.) In block 206, the system adds the average pulse data of the matched pulses to the Oscillometric Table. In block 207, the system clears the Temporary Table in preparation for the collecting of data at the next target pressure. In block 208, the system determines whether there is enough data in the Oscillometric Table to perform a blood pressure evaluation. If there is enough data in the Oscillometric Table, the system continues at block 209, else the system loops to block 201 to collect more data. In block 209, the system evaluates the Oscillometric Table. In block 210, the system determines if the evaluation was successful. If the evaluation was successful, the system continues at block 211, else the system loops to block 201 to set the cuff pressure at the next target pressure. In block 211, the system updates the screening limits for the patient and the processing for the particular blood pressure reading is complete.

Figure 3A:
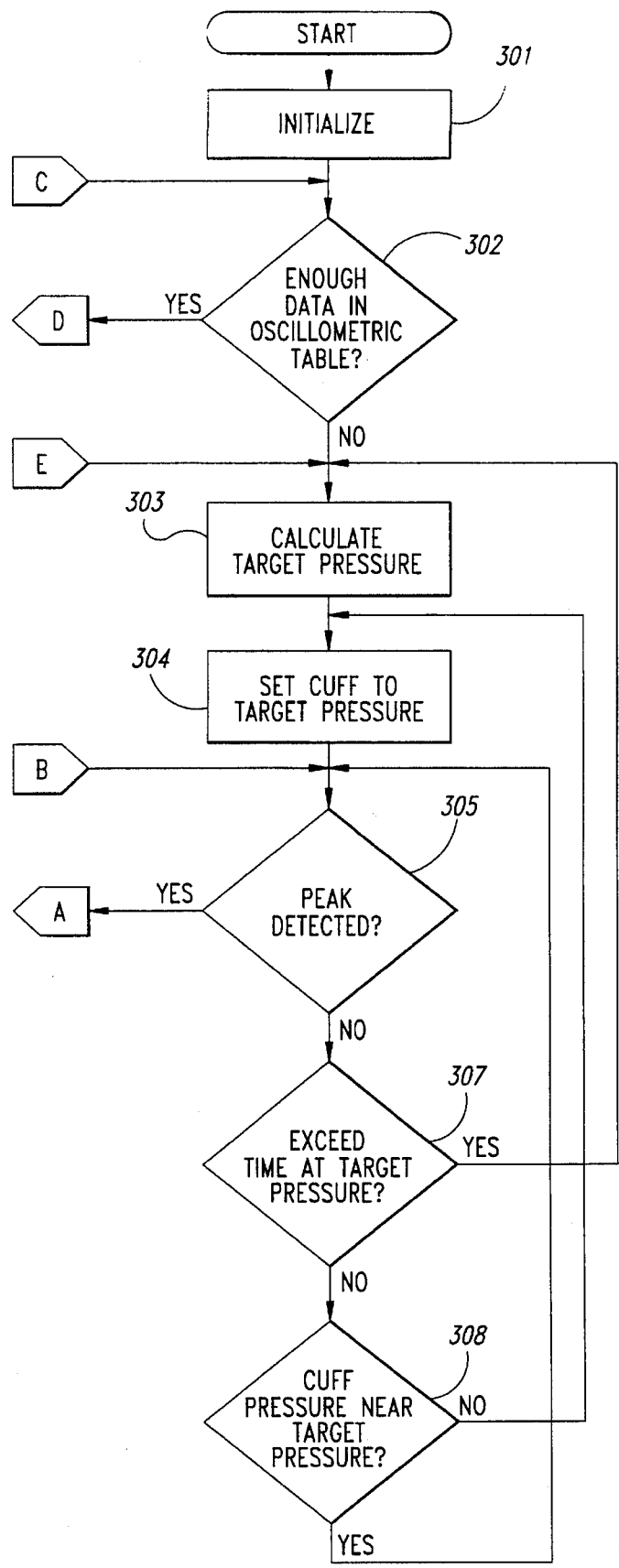
FIGS. 3A, 3B, and 3C are a detailed flow diagram of the processing routine of the present invention.
Figure 3B:
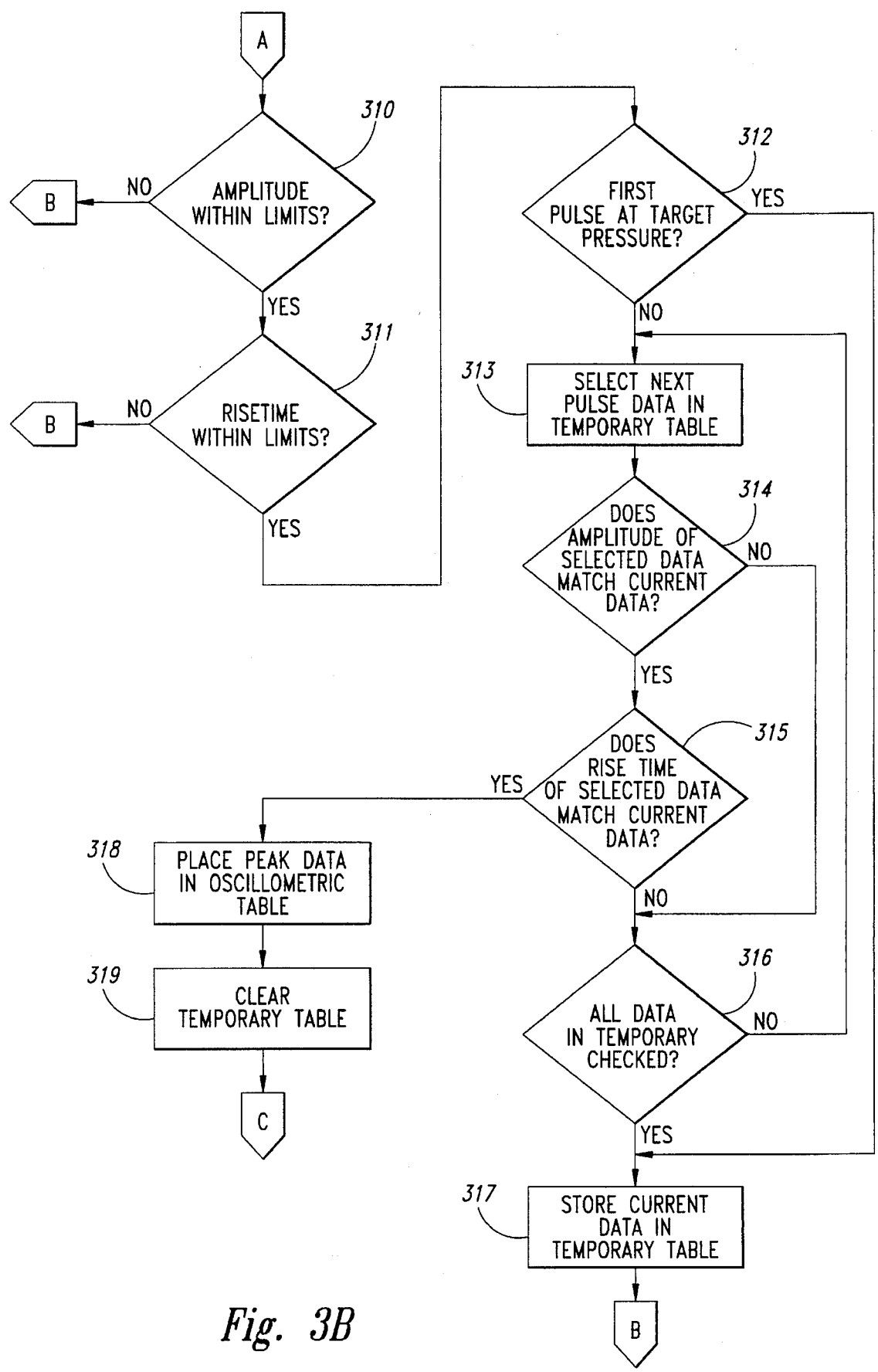
Figure 3C:
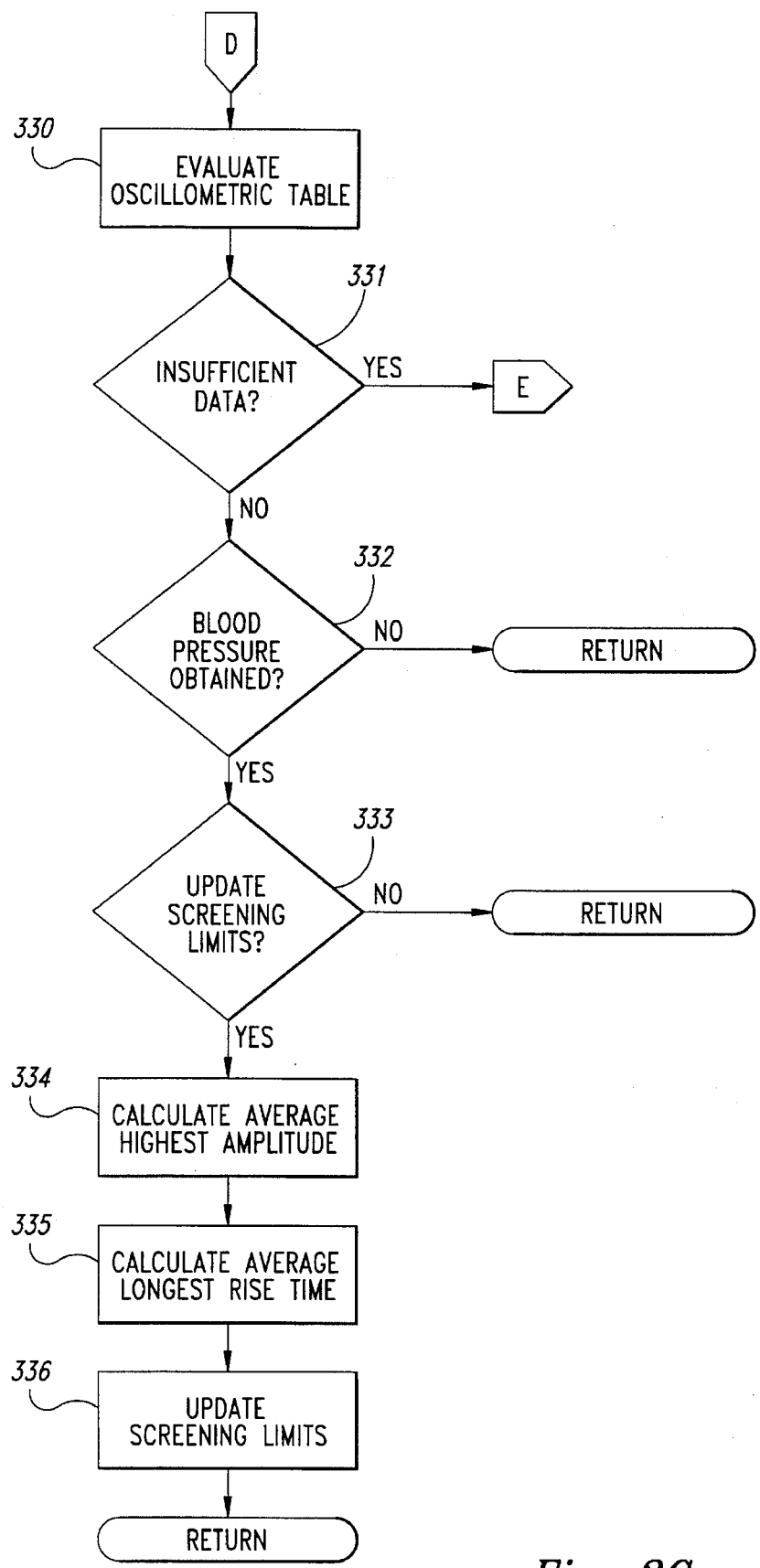

FIGS. 3A, 3B, and 3C are a detailed flow diagram of the processing routine of the present invention. The procedure that invokes this routine performs a number of conventional tasks. These tasks include, upon completion of a measurement, opening the value 20 to fully deflate the cuff 12, displaying or storing the results of the measurement, and scheduling the next automatic measurement. Also, the invoking procedure initializes the screening limits before invoking the processing routine the first time for a particular patient. In a preferred embodiment, the amplitude and rise time screening limits are set to a level that will, in effect, allow any pulse to pass through the screening test initially. The screening limits will be automatically adjusted to the patient's characteristics as described below. Referring now to FIG. 3A, in block 301, the system performs initialization for the subsequent processing. The system initializes the Temporary Table, Oscillometric Table, and various flags. In block 302, the system determines if there is enough data in the Oscillometric Table to calculate a blood pressure reading. In a preferred embodiment, there is enough data in the Oscillometric Table when there are three entries. One skilled in the art would appreciate that other criteria can be used to determine whether there is enough data in the Oscillometric Table. If there is enough data in the Oscillometric Table, the system continues at block 330 in FIG. 3C, else the system continues at block 303. In blocks 303 through 308, the system sets the cuff pressure to the target pressure and loops waiting for a peak to be detected. If a peak is detected the system continues at block 310 in FIG. 3B. In block 303, the system calculates a target pressure. In a preferred embodiment, the target pressure is initially set higher than the anticipated systolic pressure. In a preferred embodiment, each pass through block 303, the system decrements the target pressure by 8mm. However, one skilled in the art would appreciate that other methods of calculating the target pressure would be acceptable. In block 304, the system sets the cuff pressure to the target pressure. Initially, the cuff pressure starts off well below the target pressure. If the cuff pressure is below the target pressure, the system energizes the pump 18 to increase the pressure. Conversely, if the target pressure is below the cuff pressure, then the system will release pressure from the cuff 12 through the valve 20. In block 305, the system determines whether a peak has been detected. The interrupt routine, as described in FIG. 4, determines whether a peak has been detected and sets an appropriate flag. If a peak is detected, then the system continues at block 310 of FIG. 3B, else the system continues at block 307. In blocks 307 and 308, the system checks various flags that are set by the interrupt routine. These flags are used to determine whether the time at the target pressure has been too long and whether the cuff pressure is near enough to the target pressure. In block 307, if the time at the particular target pressure has been too long, then the system loops to block 303 to calculate a new target pressure and continue processing, else the system continues at block 308. In block 308, the system determines whether the cuff pressure is near the target pressure. If the cuff pressure is near the target pressure, then the system continues to wait for a peak by looping to block 305, else the system loops to block 304 to reset the cuff pressure to the target pressure.

Referring now to FIG. 3B, in blocks 310 and 311, the system determines whether the detected pulse data is within the amplitude and rise time screening limits. The screening limits are updated in block 336 of FIG. 3C. In block 310, if the amplitude of the detected pulse is within the amplitude screening limits, the system continues at block 311, else the system disregards the pulse data and loops to block 305 of FIG. 3A to wait for the next peak. In block 311, if the rise time of the detected pulse is within the rise time screening limits, then the system continues at block 312, else the system loops to block 305 in FIG. 3A to wait for the next peak.

In blocks 312 through 319, the system determines whether the detected pulse matches any other pulse data stored in the Temporary Table at the particular target pressure. If the detected pulse matches a pulse in the Temporary Table, then the system updates the Oscillometric Table and continues at block 302 of FIG. 3A to determine if there is enough data in the Oscillometric Table to be evaluated. If no match is found, then the system adds the detected pulse data to the Temporary Table and continues at block 305 in FIG. 3A to wait for the next peak. In block 312, if the detected pulse is the first pulse at the target pressure to pass the screening limits, then there is no data in the Temporary Table to match and the system continues at block 317, else the system continues at block 313. In blocks 313 through 316, the system loops comparing the detected pulse with each of the entries in the Temporary Table. If a match is found, the system continues at block 318. In block 313, the system selects the next pulse in the Temporary Table starting with the last pulse stored in the table. In block 314, the system determines whether the amplitude of the selected pulse matches the amplitude of the detected pulse. In a preferred embodiment, the amplitude of two pulses match when the absolute value of their differences is less than or equal to a constant value plus 9% of the amplitude of the detected pulse. In a preferred embodiment, the constant is set to account for the inherent noise in the detection equipment. One skilled in the art would appreciate that although amplitudes preferably match when they are within 9%, other matching criterions are acceptable. If an amplitude match is found, the system continues at block 315, else the system continues at block 316. In block 315, the system determines whether the rise time of the selected pulse matches the rise time of the detected pulse. In a preferred embodiment, the rise times of pulses match when they are within approximately 8 milliseconds. One skilled in the art would appreciate that other rise time matching criteria would produce acceptable results. If the rise times match, then the system continues at block 318, else the system continues at block 316. In block 316, if all the data in the Temporary Table has been checked for a match, then the system continues at block 317, else the system loops to block 313 to select the next pulse in the Temporary Table. In block 317, no match has been found, and the system stores the detected pulse data in the Temporary Table and continues at block 305 of FIG. 3A to wait for the next peak. In block 318, the system places the matched pulse data in the Oscillometric Table. In a preferred embodiment, the average value of the amplitude and rise times and associated cuff DC pressure for the selected and detected pulses are stored in the Oscillometric Table. The time interval between the two matching pulses is also stored to be used to determine the heart rate. In block 319, the system clears the Temporary Table for processing at the next target pressure level, and the system continues at block 302 of FIG. 3A to determine if there is enough data in the Oscillometric Table for evaluation.

Referring to FIG. 3C, in block 330, the system evaluates the Oscillometric Table to determine the systolic and diastolic blood pressures. Three outcomes of this evaluation are possible. First, the evaluation was incomplete because of insufficient data. Second, the evaluation found data inconsistencies although there was sufficient data. During evaluation, each amplitude and heart rate interval in the Oscillometric Table is checked for internal consistency with the other entries. These checks are fully described in the earlier cited patents. Third, the evaluation was successful. In block 331, if the data is insufficient, then the system loops to block 303 in FIG. 3A to collect additional data at the next lower target pressure, else the system continues at block 332. In block 332, if inconsistencies with the data are found, then the system returns with an error code, else the system continues at block 333. In block 333, the system determines whether the screening limits should be updated. In a preferred embodiment, the screening limits should not be updated when too many pulses fail to pass the screening limits or when too many nonmatching pulses were detected. This test ensures that the screening limits are set as a function of the patient oscillometric data rather than as a function of artifacts. In alternate embodiments, the screening limits are updated when a majority of the pulses fall outside the screening limits. If the screening limits are to be updated, the system continues at block 334, else the system returns. In block 334, the system calculates the average highest amplitude for several blood pressure readings. In block 335, the system calculates the average longest rise time for several blood pressure readings. In block 336, the system updates the screening limits based on the average highest amplitude and the average longest rise time. In a preferred embodiment, the maximum amplitude screening limit is set to 150% of the average highest amplitude, and the minimum amplitude screening limit is set to 19% of the average highest amplitude. In a preferred embodiment, the maximum rise time screening limit is set to 20 milliseconds longer than the average longest rise time. There is no minimum rise time screening limit. In a preferred embodiment, the averages are calculated using the last five blood pressure measurements that resulted in an update of the screening limits. One skilled in the art would appreciate that the updating of these screening limits can be varied and still produce acceptable results. The system then returns.

Figure 4:
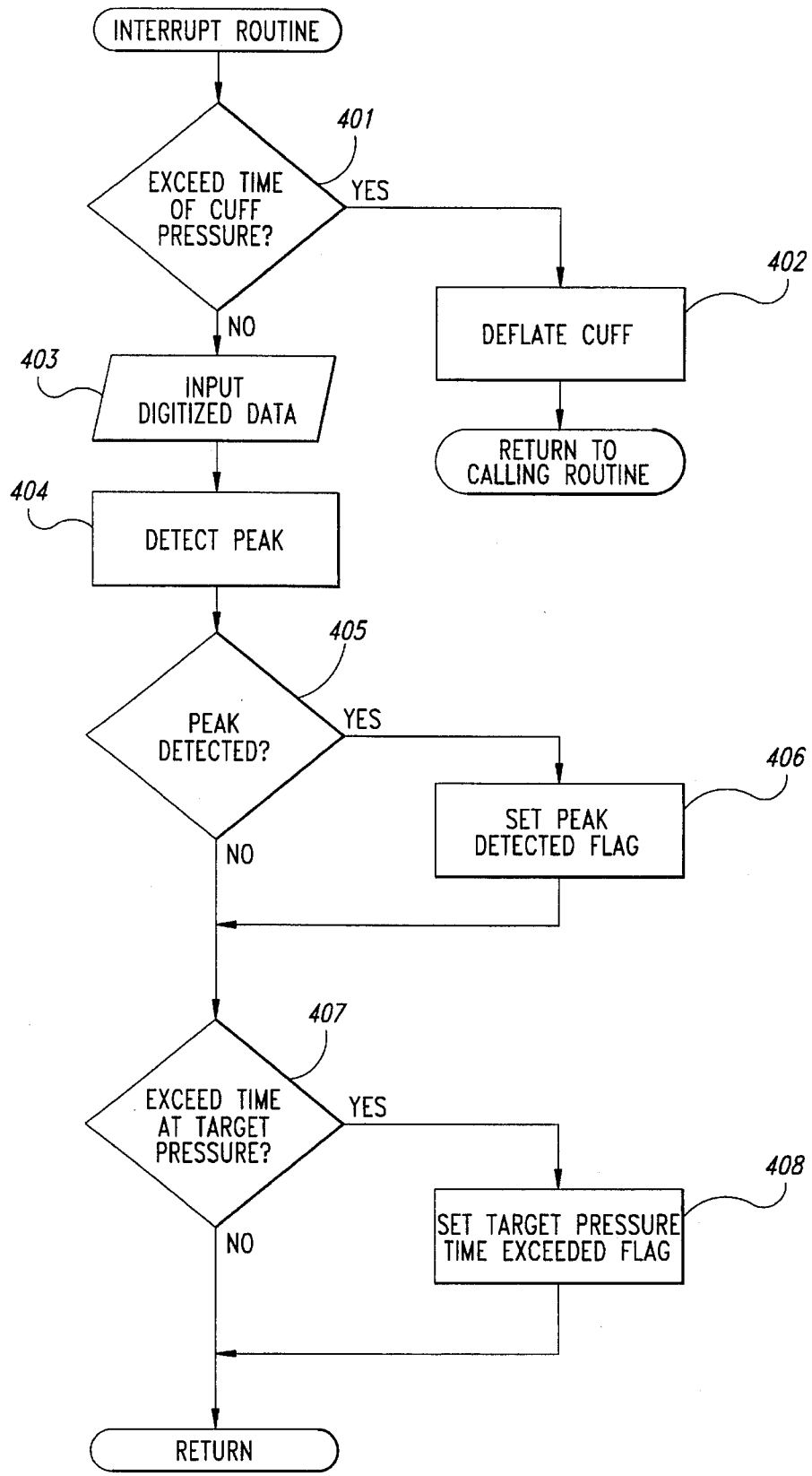
FIG. 4 is a flow diagram of the interrupt routine.

FIG. 4 is a flow diagram of the interrupt routine. The interrupt is timer-driven. The interrupt routine inputs digitized data, detects when a peak occurs, and checks for timing and pressure measurements. The interrupt routine sets flags that are used by the main processing routine for detection of certain conditions. Because of the potential danger to a patient, the interrupt routine first determines whether the allowed time to have the cuff pressurized is exceeded. In block 401, if the time is exceeded, the routine continues at block 402, else the routine continues at block 403. In block 402, the routine deflates the cuff and returns to the calling routine, rather than the interrupted routine. In block 403, the routine inputs the digitized AC oscillometric pressure and the DC cuff pressure and initiates the next sampling by the A/D converter. In block 404, the routine determines if a peak occurred. A peak occurs when the data has passed from below a high trigger level to above the high trigger level, and then passes from above a low trigger level to below the low trigger level. One skilled in the art would appreciate that other peak detection algorithms would produce acceptable results. In block 405, if a peak was detected, then the routine sets the peak detected flag in block 406. In block 407, if the time at the target pressure has exceeded a predetermined time, then the routine sets the target pressure time exceeded flag. The routine stores the raw digitized data, and the main processing routine calculates the amplitude and rise time. In a preferred embodiment, the rise time is the amount of time it takes the pressure to rise between 25% and 88% of the pulse amplitude. The routine then returns to the interrupted routine.

Although the present invention has been described in terms of preferred embodiments, it is not intended that the invention be limited to these embodiments. Modification within the spirit of the invention will be apparent to those skilled in the art. The scope of the present invention is defined by the claims that follow.

I claim:

1. A blood pressure monitor, comprising:

a blood pressure cuff;

an air pressure pump pneumatically coupled to the blood pressure cuff;

a valve pneumatically coupled to the blood pressure cuff;

a pressure transducer pneumatically coupled to the blood pressure cuff, the pressure transducer generating a signal indicative of air pressure in the blood pressure cuff and a signal corresponding to the oscillometric pulses in the blood pressure cuff;

processor means connected to the pressure transducer and receiving the signal indicative of the air pressure in the blood pressure cuff and the signal corresponding to oscillometric pulses in the blood pressure cuff, the processor means connected to the air pressure pump and the valve, the processor means comprising means for energizing the air pump and valve to vary the air pressure in the blood pressure cuff, detecting an occurrence of an oscillometric pulse, determining an amplitude and a time related characteristic of the oscillometric pulse, determining whether the amplitude and the time related characteristic of the oscillometric pulse are within respective amplitude and time related screening limits, disregarding the pulse when the amplitude and time related characteristics of the oscillometric pulse are not within the respective screening limits, determining whether the screened pulse has an amplitude and time related characteristics that bear a predetermined relationship to the amplitude and the same time related characteristics of another screened pulse detected at a cuff air pressure level, saving pulse data when pulses match, and determining systolic and diastolic pressures based on the saved pulse data.

2. The blood pressure monitor of claim 1 further including means for updating the characteristic screening limits based on data specific to a patient.

3. The blood pressure monitor of claim 1 wherein a match between screened pulses is determined by means for comparing the time related characteristics of screened pulses detected at substantially the same cuff pressure.

4. The blood pressure monitor of claim 1 wherein said processor means establishes the time related screening limit based on an average of the time related characteristics of a plurality of oscillometric pulses obtained during a plurality of previous blood pressure readings for the patient.

5. The blood pressure monitor of claim 1 wherein the processor means determines whether the screened pulse matches another pulse by comparing the screened pulse with a pulse other than the immediately previous pulse screened.

6. The blood pressure monitor of claim 1 wherein the processor means determines the time related characteristic of the oscillometric pulse by determining the rise time of the oscillometric pulse.

7. The blood pressure monitor of claim 1 further including means for updating the characteristic screening limits based on the characteristics of a plurality of previously detected pulses.

8. A system for calculating blood pressure from a plurality of oscillometric pulses detected at a plurality of pressures, comprising:

first means for determining whether an amplitude and a time related characteristic of each oscillometric pulse is within respective screening limits;

second means for disregarding the oscillometric pulse when the amplitude and the time related characteristics of the pulse are not within the respective screening limits;

third means for saving pulse data corresponding to the oscillometric pulse when the amplitude and the time related characteristics of the pulse are within the respective screening limits;

fourth means for calculating blood pressure parameter based on the saved pulse data; and fifth means for updating the respective screening limit based on the amplitude and the time related characteristic of a plurality of previously detected pulses.

9. The system of claim 8 further including means for updating the characteristic screening limits based on data specific to a patient.

10. The system of claim 8 wherein the first means bases the time related screening limit on an average of the time related characteristics of a plurality of oscillometric pulses obtained during a plurality of previous blood pressure readings for the patient.

11. The system of claim 8 wherein the first means determines the time related characteristic of the oscillometric pulse by determining the rise time of an oscillometric pulse.

* * * * *